(12) United States Patent
Malhotra et al.

(10) Patent No.: US 10,039,752 B2
(45) Date of Patent: Aug. 7, 2018

(54) METHAZOLAMIDE FOR THE TREATMENT OF CANCER

(71) Applicant: Cipla Limited, Mumbai (IN)

(72) Inventors: Geena Malhotra, Mumbai (IN); Kalpana Joshi, Maharashtra (IN); Jeevan Ghosalkar, Thane (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/651,060

(22) Filed: Jul. 17, 2017

(65) Prior Publication Data

US 2018/0021313 A1    Jan. 25, 2018

(30) Foreign Application Priority Data

Jul. 21, 2016  (IN) .............................. 201621024984

(51) Int. Cl.
| | | |
|---|---|---|
| *A61K 31/41* | (2006.01) | |
| *A61K 31/433* | (2006.01) | |
| *A61K 31/155* | (2006.01) | |
| *A61K 35/39* | (2015.01) | |
| *A61K 45/06* | (2006.01) | |

(52) U.S. Cl.
CPC .......... *A61K 31/433* (2013.01); *A61K 31/155* (2013.01); *A61K 35/39* (2013.01); *A61K 45/06* (2013.01)

(58) Field of Classification Search
CPC .................................................. C07D 285/135
USPC ........................................................... 514/363
See application file for complete search history.

(56) References Cited

U.S. PATENT DOCUMENTS

| | | | |
|---|---|---|---|
| 6,214,381 B1* | 4/2001 | Burklow ............... | A61K 9/2054 424/457 |
| 2012/0114670 A1* | 5/2012 | Land .................... | A61K 31/365 424/174.1 |
| 2015/0150855 A1* | 6/2015 | Walder ................. | A61K 31/433 514/363 |
| 2015/0174108 A1* | 6/2015 | Walder ................. | A61K 31/433 514/363 |

* cited by examiner

*Primary Examiner* — Raymond J Henley, III
(74) *Attorney, Agent, or Firm* — Meunier Carlin & Curfman LLC

(57) ABSTRACT

The present invention relates to methods of using methazolamide to treat pancreatic cancer. Pancreatic cancer can be treated by administering to a patient in need thereof an effective amount of methazolamide, optionally in combination with one or more additional cancer therapies.

19 Claims, 6 Drawing Sheets

METHAZOLAMIDE FOR THE TREATMENT OF CANCER

CROSS REFERENCE TO RELATED APPLICATION

This application claims the benefit of Indian Application 201621024984, filed on Jul. 21, 2016, the contents of which are incorporated herein in its entirety.

FIELD OF THE INVENTION

The present invention relates to a method of treatment of cancer, specifically pancreatic cancer. In particular, the present invention pertains to methods for the treatment of pancreatic cancer by administering methazolamide alone or in combination with one or more additional cancer therapies.

BACKGROUND

Pancreatic cancer is an aggressive and highly lethal form of pancreatic malignancy. The incidence of pancreatic cancer varies greatly across regions with the highest incidence and mortality rates found in developed countries. Approximately, over 2 million people worldwide die annually due to pancreatic cancer along with a steady increasing incidence rate. Deaths from pancreatic cancer rank fourth among cancer-related deaths in the United States and it is one of the most common gastrointestinal malignancies.

Risk factors for pancreatic cancer include, among others, high-fat diet, smoking, chronic pancreatitis, primary sclerosing cholangitis, hereditary pancreatitis, family history of pancreatic cancer and diabetes mellitus. However, age seems to be a significant risk factor, and the rate of incidence is proportional with the age of the individual. Pancreatic cancer possesses some characteristics such as fast progress, high degree of malignancy and early metastasis which eventually brings poor prognosis for patients with a 5-year survival rate of only 1% to 3%.

Approximately 20% of patients are diagnosed with localized and potentially curable tumors. However, majority (95%) of the cases of pancreatic cancer are adenocarcinomas which resemble the pancreatic ductal cell. Metastasis of this cancer is generally local, most often involving the liver, lung, spleen, lymphatic system, adrenal glands and transverse colon.

Pancreatic cancer is treated in several ways, either alone or in combination based upon the stages of malignancy. Currently, surgery or resection is still the most basic means for treating pancreatic cancer for curative treatment. However, despite the fact that surgical options for pancreatic cancer are now associated with acceptable outcomes, they often prove ineffective in controlling the disease with reported recurrence rates approaching almost 80% (both locally and distant) and a 5-year survival rate of only 10%-24% for cases involving total resection.

Other treatment options of pancreatic cancer range from systemic chemotherapy alone to combined forms of treatment with chemoradiation and chemotherapy. Chemotherapy treatments can be categorized as adjuvant (treatment after surgery), neo-adjuvant (treatment prior to surgery) and palliative. The most common chemotherapeutic agents that are used to treat pancreatic cancer are gemcitabine, 5-fluorouracil, capecitabine, cisplatin and oxaliplatin. These agents function on the basis of cross-linking mechanisms in which their reactive region interacts with the cell's DNA or RNA nucleotides, thus disrupting the cell cycle progression which leads to cancer cell apoptosis.

Further, targeted therapy of erlotinib in combination with gemcitabine has been approved for patients with advanced pancreatic cancer. Targeted therapy is a treatment that targets the cancer's specific genes, proteins or the tissue environment that contribute to cancer growth and survival. This type of treatment blocks the growth and spread of cancer cells while limiting damage to healthy cells.

Although some progress has been made in the management of pancreatic cancer over the years, the benefits from such treatments are considerably small and have always been confined to a minority of the treated population. Further, aggressive tumor biology and limited efficacy of conventional therapies have led to rapid progression of this disease as well as an increase in the cancer specific mortality rate. Hence, there still remains a need to develop different treatment approaches in a cost effective and a time efficient manner.

SUMMARY

Disclosed herein are methods of treating pancreatic cancer by administering methazolamide. The methazolamide may be administered in combination with one or more additional cancer therapies. In some instances, methazolamide may be administered in combination with one or more cancer chemotherapeutic agents.

Also disclosed herein are pharmaceutically acceptable compositions containing methazolamide, in some cases in combination with one or more anti-cancer drugs for the treatment of pancreatic cancer.

The details of one or more embodiments are set forth in the descriptions below. Other features, objects, and advantages will be apparent from the description and from the claims.

DETAILED DESCRIPTION

Figure 1:
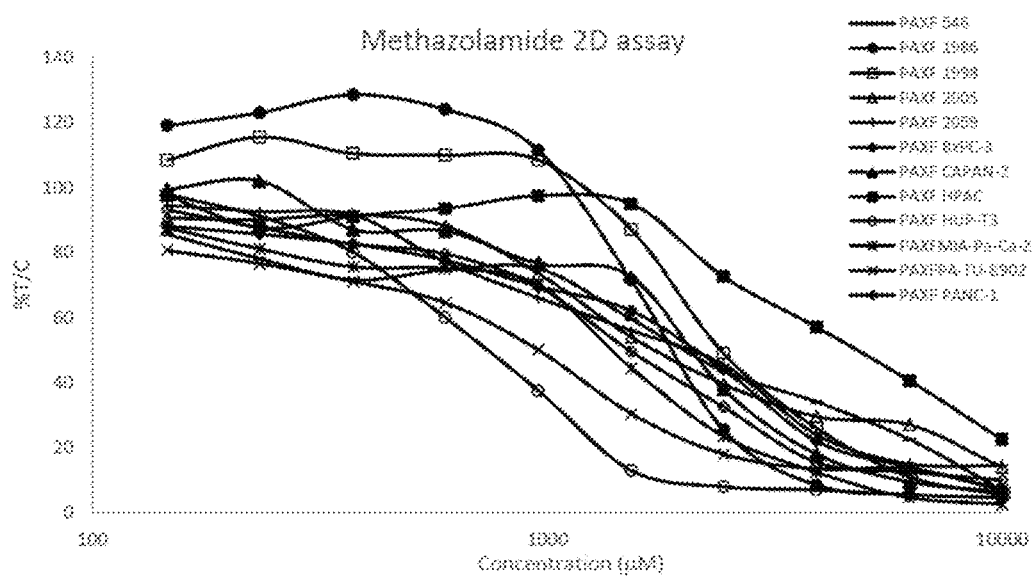
FIG. 1 depicts a concentration-effect curve exhibiting efficacy of methazolamide in human tumor cell models.
Figure 2:
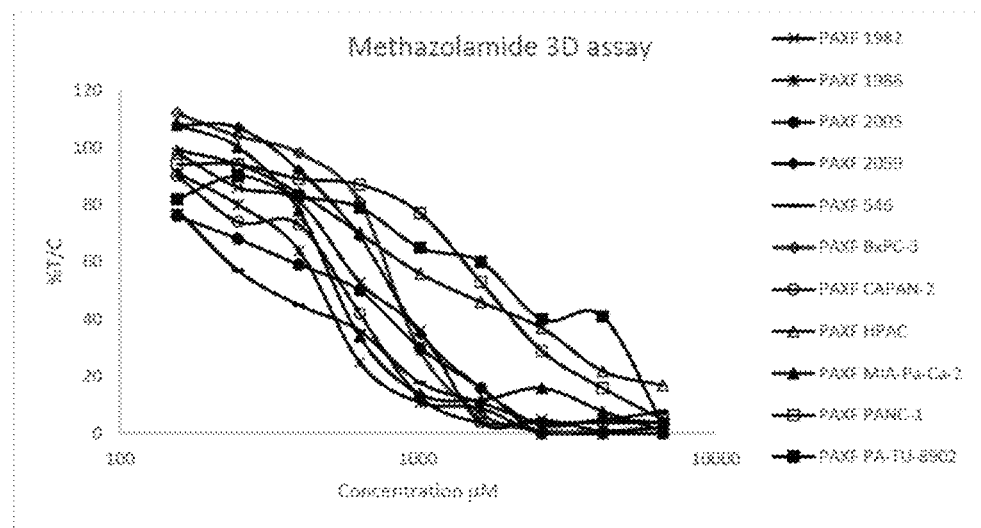
FIG. 2 depicts a concentration-effect curve exhibiting efficacy of methazolamide in human tumor models.
Figure 3:
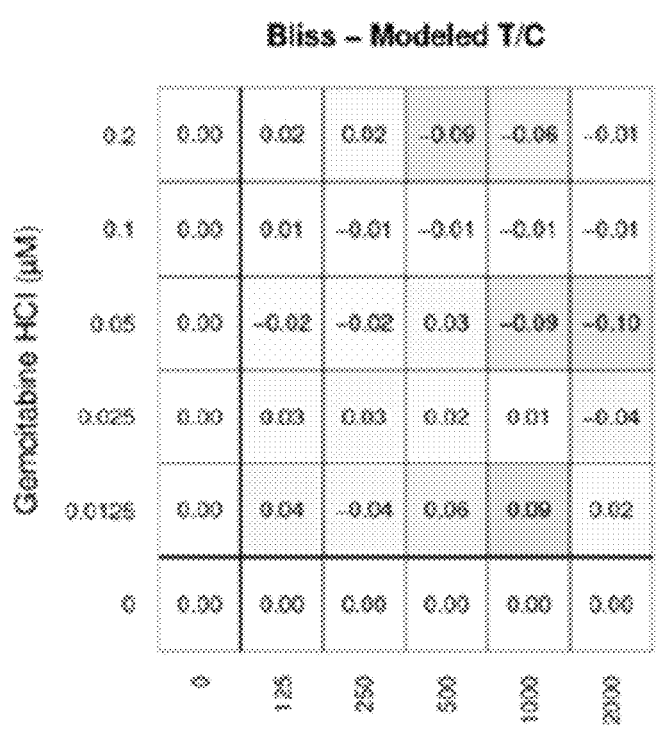
FIG. 3 includes a depiction of the anti-tumor efficacy of methazolamide in combination with gemcitabine against cell line PAXF 1986L. Bliss index indicates the difference of Bliss neutral and modeled T/C for each pair of conditions. Where positive values (Bliss Index ≥0.15) indicate synergism, negative values (Bliss Index ≤−0.15) indicate antagonism, and zero is the neutral value.
Figure 4:
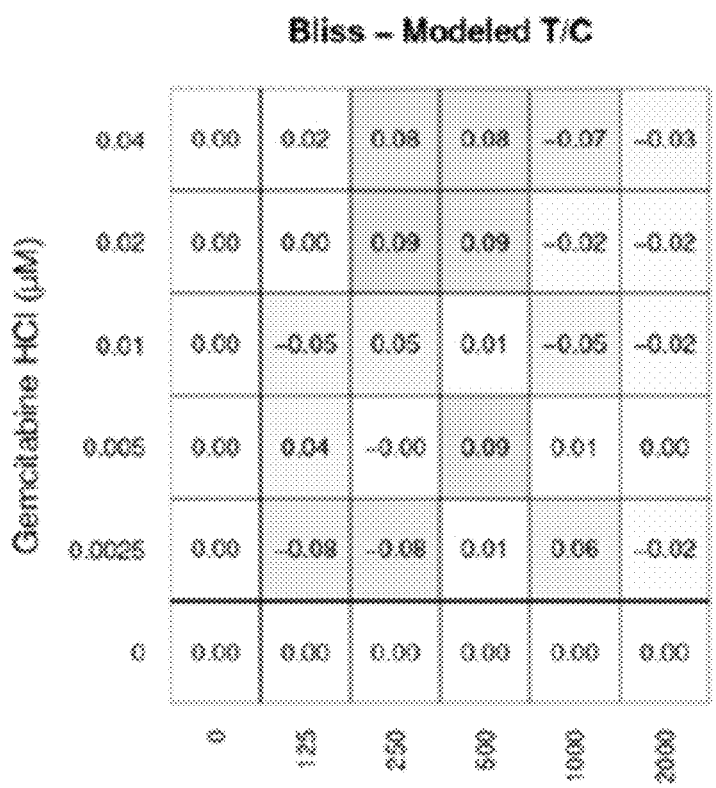
FIG. 4 includes a depiction of the anti-tumor efficacy of methazolamide in combination with gemcitabine against cell line PAXF 546L. Bliss index indicates the difference of Bliss neutral and modeled T/C for each pair of conditions. Where positive values (Bliss Index ≥0.15) indicate synergism, negative values (Bliss Index ≤−0.15) indicate antagonism, and zero is the neutral value.
Figure 5:
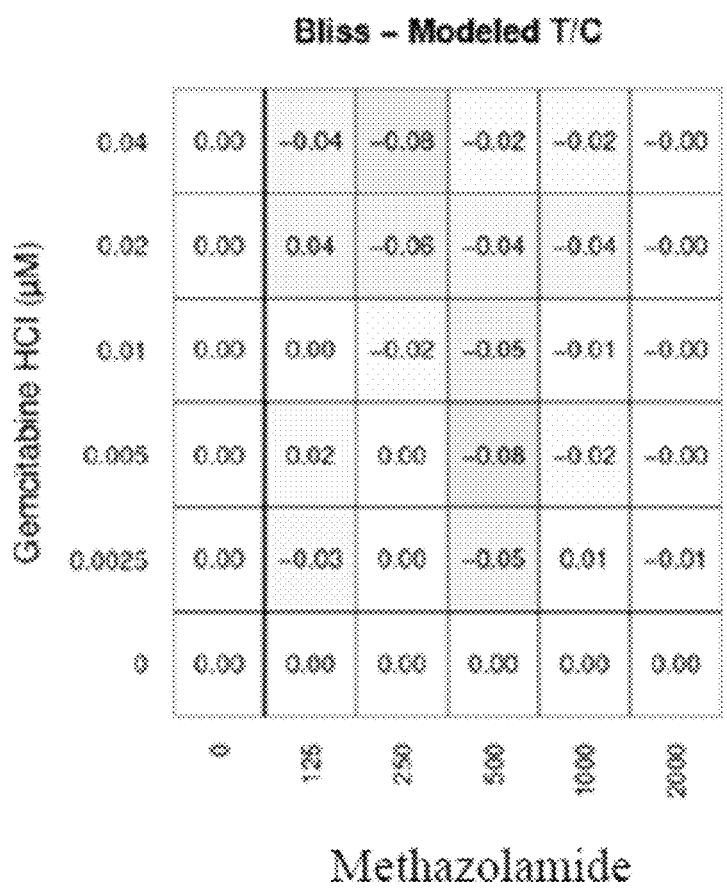
FIG. 5 includes a depiction of the anti-tumor efficacy of methazolamide in combination with gemcitabine against cell line PAXF Capan-2. Bliss index indicates the difference of Bliss neutral and modeled T/C for each pair of conditions. Where positive values (Bliss Index ≥0.15) indicate synergism, negative values (Bliss Index ≤−0.15) indicate antagonism, and zero is the neutral value.
Figure 6:
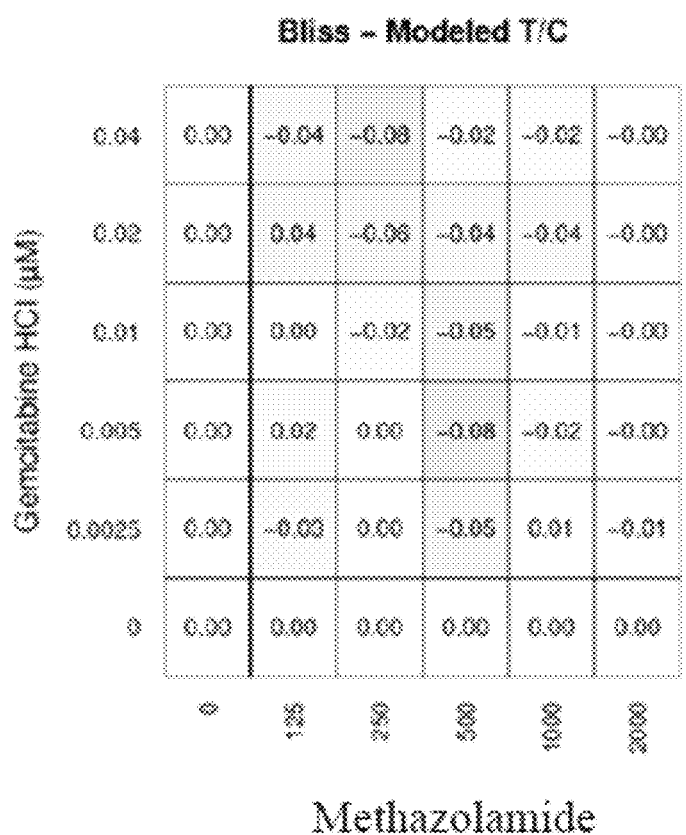
FIG. 6 includes a depiction of the anti-tumor efficacy of methazolamide in combination with gemcitabine against cell line PAXF MIA-Pa-Ca-2. Bliss index indicates the difference of Bliss neutral and modeled T/C for each pair of conditions. Where positive values (Bliss Index ≥0.15) indicate synergism, negative values (Bliss Index ≤−0.15) indicate antagonism, and zero is the neutral value.
Figure 7:
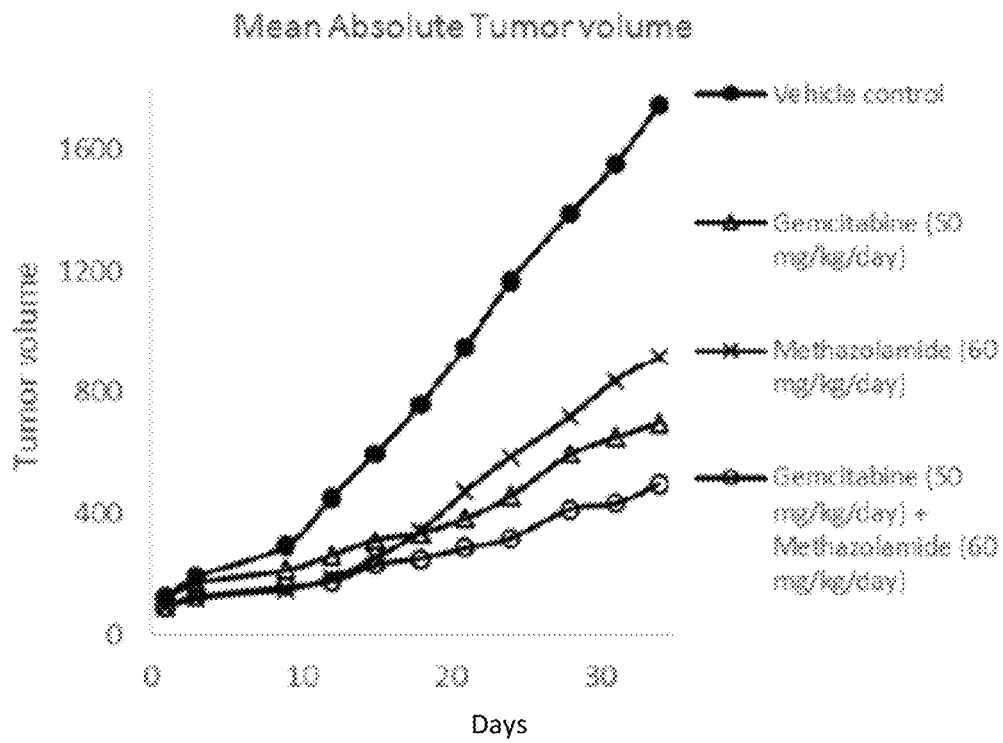
FIG. 7 depicts in vivo anti-tumor efficacy using PDX model PAXF 546. Includes a graphical representation of mean tumor volume across the animal group populations using vehicle, gemcitabine, methazolamide, and methazolamide+gemcitabine.
Figure 8:
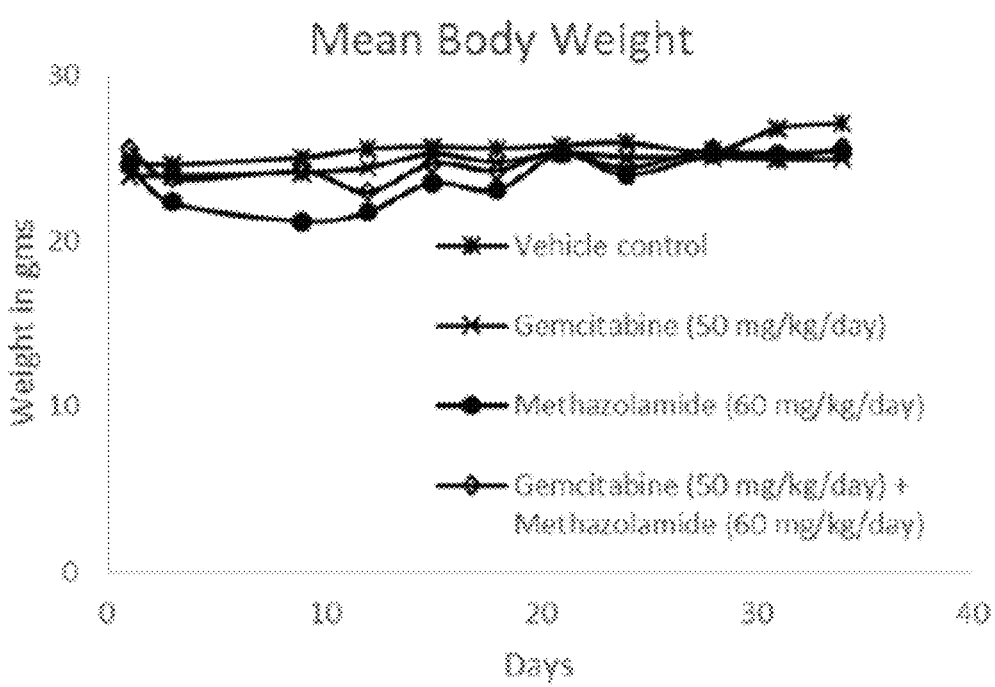
FIG. 8 depicts in vivo anti-tumor efficacy using PDX model PAXF 546. Includes a graphical representation depicting change in body weights across the animal group population using vehicle, gemcitabine, methazolamide, and methazolamide+gemcitabine.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes- from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Pancreatic cancer is one of the most common cancer that affects the exocrine pancreas and further is one of the most difficult cancer to treat. In pancreatic cancer, aberrations can occur in signal transduction and other pathways that promote cell survival and allow proliferation. These include hepatocyte growth factor (HGF), KRAS, PI3K/Akt/mTOR, EGFR, insulin-like growth factor (IGF-1) (which is co-expressed with Src) and vascular endothelial growth factor (VEGF).

The inventors of the present invention have found that methazolamide exhibits a significant role in the inhibition of pancreatic tumor growth, progression and metastasis.

Methazolamide can be chemically described as N-[5-(aminosulfonyl)-3-methyl-1,3,4-thiadiazol-2(3H)-ylidene] acetamide and is represented as:

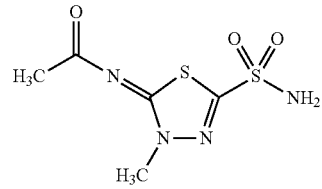

Methazolamide is currently indicated in the treatment of ocular conditions wherein the lowering of intraocular pressure is likely to be of therapeutic benefit, such as chronic open-angle glaucoma, secondary glaucoma and preoperatively in acute angle-closure glaucoma wherein the lowering of intraocular pressure is desired before surgery.

Methazolamide is currently available under the trade name Neptazane® 25 mg and 50 mg tablets. The effective therapeutic dose of Neptazane® varies from 50 mg to 100 mg two or three times daily.

The term "methazolamide" used in context of the present invention is used in broad sense to include not only "methazolamide" per se but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

Methazolamide may be formulated as a pharmaceutically acceptable salt. Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Methazolamide may be formulated as pharmaceutically acceptable prodrugs. Prodrugs can substantially increase the bioavailability of the compounds, permitting more effective oral therapy. The primary sulfonamide may be modified to improve properties, for instance as a $N—C_1-C_{10}$ acyl, $N—C_1-C_{10}$ alkoxycarbonyl, N-sulfonyl urea, N-sulfonylimidate and the like.

There is provided a method of alleviating or treating pancreatic cancer by administration of methazolamide optionally in combination with one or more anti-cancer drugs either simultaneously, sequentially, or separately. The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. As used herein, the term "delay" refers to methods that reduce the probability of disease development/extent in a given time frame, when compared to otherwise similar methods that do not include the use of methazolamide. Probabilities can be established using clinical trials, but can also be determined using in vitro assays when correlations have been established.

In certain embodiments, administration of methazolamide can reduce tumor volume. For instance, methazolamide can be administered in an amount effective to reduce pancreatic tumor volume by at least 10%, 20%, 30%, 40%, 50%, 60%, 70%, 80%, or 90%. In some embodiments, methazolamide can inhibit pancreatic cancer cell proliferation. For instance, methazolamide can be administered in an amount effective to inhibit at least about 10%, 20%, 30%, 40%, 60%, 70%, 80%, 90%, or 100% of cell proliferation. In some embodiments, methazolamide can inhibit pancreatic cancer metastasis. For instance, methazolamide can be administered in an amount effective to inhibit at least about 10%, 20%, 30%, 40%, 60%, 70%, 80%, 90%, or 100% of metastasis.

Methazolamide can be administered according to various dosing regimens. For instance, methazolamide can be administered once a day, twice a day, three times per day, or even more than three times a day. The methazolamide can be administered such that the total daily dose is at least 50 mg, at least 100 mg, at least 250 mg, at least 500 mg, at least 750 mg, at least 1,000 mg, at least 1,250 mg, at least 1,500 mg, at least 1,750 mg, or at least 2,000 mg. In some instances, the total daily dose can be from 5-5,000 mg, 10-5,000 mg, 25-5,000 mg, 50-5,000 mg, 100-5,000 mg, 200-2,500 mg, 500-2,500 mg, 10-2,500 mg, 50-2,500 mg, 100-2,500 mg, 100-2,000 mg, 250-2,000 mg or 500-2,000 mg. In other embodiments, methazolamide can be administered less than once daily, instance, once every two days, once every three days, once every five days, once every seven days, once every ten days, once every fourteen days, once every twenty-eight days or once every month. Methazolamide can be administered by other intermittent therapies as well, for instance 2 days on, 1 day off, e.g. "2/1." Other on/off sequences that can be employed include 3/1; 3/2; 4/1; 5/1; 5/2; 5/3; 5/4; 6/1; 6/5; 7/1; 7/2; 7/3; 7/4; 7/5; 7/6; 8/1; 8/3; 8/5; 8/7; 9/1; 9/2; 9/4; 9/5; 9/7; 9/8; 10/1; 10/3; 10/7; and 10/9.

According to the present invention, there is provided a use of methazolamide in combination with one or more anti-cancer drugs either simultaneously, sequentially, or separately for the treatment of pancreatic cancer. In certain cases, methazolamide can be administered for a period of at least 1 week, at least 2 weeks, at least 4 week, at least 6 weeks, at least 8 week, or at least 10 weeks, prior to commencing treatment with additional agents. In some instances, methazolamide and the other agent can be administered intermittently, for instance a period of methazolamide administration, followed by a period in which the other agent to administered, followed by another period of methazolamide administration. The cycle can be repeated as many times as necessary.

In certain cases, the combination of methazolamide and additional agent will exhibit a greater than additive effect (i.e., a synergistic effect). In other instance, the use of methazolamide permits a reduced amount of the other agent to be administered, without a corresponding decrease in therapeutic efficiency.

Preferably, one or more anti-cancer drugs that may be envisaged under the scope of the present invention may comprise currently approved targeted anti-cancer drugs for the treatment of pancreatic cancer such as, but not limited to, a nucleoside analogue, antifolate, antimetabolite, topoisomerase I inhibitor, anthracycline, podophyllotoxin, taxanes, vinca alkaloid, alkylating agent, platinum compound, proteasome inhibitor, nitrogen mustard, oestrogen analogue, monoclonal antibody, tyrosine kinase inhibitor, mTOR inhibitor, retinoid, immunomodulatory agent, histone deacetylase inhibitor, other kinase inhibitor, metabolic inhibitors, and microtubule inhibitors. Exemplary anti-cancer drugs that can be used in combination with methazolamide include, everolimus, erlotinib, gemcitabine, 5-fluorouracil, capecitabine, cisplatin, paclitaxel and oxaliplatin. Most preferably, the anti-cancer drug is gemcitabine.

In cases of combination therapy, it is possible that a unitary dosage form comprising both methazolamide and one or more additional anti-cancer drugs may be employed. In some instances, the combinations may be provided in form of kit preparation wherein methazolamide is present in an oral or parenteral composition and the additional anti-cancer drug therapy may be provided in an oral or parenteral composition. In one embodiment, the kit preparation may be provided in an all oral dosage form presentation wherein both the methazolamide and the additional anti-cancer drug are presented in an oral dosage form. In another embodiment, the kit preparation may be provided as an oral plus parenteral dosage form presentation wherein methazolamide is presented in an oral form and the additional anti-cancer drug is presented in a parenteral form. Alternatively, the kit preparation may be provided wherein methazolamide is presented in a parenteral form and the additional anti-cancer drug is presented in an oral dosage form.

In some instances, methazolamide can be used in combination with ionizing radiation, ablation therapy, embolization therapy, and/or surgical interventions for the treatment of pancreatic cancer. Methazolamide can be administered before, during, or after treatment with ionizing radiation or surgical intervention. In certain cases, methazolamide can be administered for a period of at least 1 week, at least 2 weeks, at least 4 week, at least 6 weeks, at least 8 week, or at least 10 weeks, prior to commencing treatment with ionizing radiation or surgery. Exemplary forms of radiation include x-rays, gamma rays, electron beams and proton beams. Administration of methazolamide can permit a reduction in the total exposure of the patient to ionizing radiation, without a corresponding reduction in therapeutic efficiency. In certain instances, methazolamide can be administered both prior and subsequent to ionizing radiation and/or surgical interventions.

The present inventors have discovered the methazolamide is surprisingly effective for the treatment of pancreatic cancer at various stages. The TNM (tumor size/lymph node/metastasis) system is used in conjunction with a number to include the severity of the cancer; higher numbers indicate the cancer is more advanced. The TNM system includes the following stages of pancreatic cancer:

Stage 0: The tumor is confined to the top layers of pancreatic duct cells and has not invaded deeper tissues. It has not spread outside of the pancreas. These tumors are sometimes referred to as pancreatic carcinoma in situ or pancreatic intraepithelial neoplasia III (PanIn III).

Stage IA: The tumor is confined to the pancreas and is 2 cm across or smaller (T1). The cancer has not spread to nearby lymph nodes (N0) or distant sites (M0).

Stage IB: The tumor is confined to the pancreas and is larger than 2 cm across (T2). The cancer has not spread to nearby lymph nodes (N0) or distant sites (M0).

Stage IIA: The tumor is growing outside the pancreas but not into major blood vessels or nerves (T3). The cancer has not spread to nearby lymph nodes (N0) or distant sites (M0).

Stage IIB: The tumor is either confined to the pancreas or growing outside the pancreas but not into major blood vessels or nerves. The cancer has spread to nearby lymph nodes (N1) but not to distant sites (M0).

Stage III: The tumor is growing outside the pancreas and into nearby major blood vessels or nerves (T4). The cancer may or may not have spread to nearby lymph nodes (Any N). It has not spread to distant sites (M0).

Stage IV: The cancer has spread to distant sites (M1).

Methazolamide can be used to treat Stage 0 pancreatic cancer, Stage I pancreatic cancer, Stage II pancreatic cancer Stage III pancreatic cancer, or Stage IV pancreatic cancer. In some embodiments, methazolamide can reduce tumor size, inhibit tumor growth, alleviate symptoms, delay progression, prolong survival, including, but not limited to disease free survival, prevent or delay pancreatic cancer metastasis, reduce or eliminate preexisting pancreatic cancer metastasis, and/or prevent recurrence of pancreatic cancer. In certain embodiments, methazolamide can be administered to a treatment-naïve patient, i.e., a patient that has not yet undergone a course of therapy with a different chemotherapeutic agent. In other embodiments, methazolamide can be administered to a patient who has already received one or more courses of chemotherapy. In some embodiments, the patient can have recurrent pancreatic cancer, or pancreatic cancer that is refractory to one or more therapies.

In some embodiments, the one or more chemotherapies includes gemcitabine, for instance gemcitabine monotherapy. In some embodiments, the prior chemotherapy include administration of gemcitabine and erlotinib, gemcitabine and capecitabine, gemcitabine and 5-FU, or gemcitabine, erlotinib, capecitabine, and/or 5-FU. In some embodiments, the prior therapy is adjuvant gemcitabine therapy. The prior chemotherapy can have been given for at least 1, 2, 3, 4, 5, 6, 7, 8, 9, 10, 11, or 12 months prior to commencement of methazolamide therapy. In certain embodiments, methazolamide can be added to any of the foregoing treatment regimens without discontinuing the earlier treatment.

Preferably, methazolamide may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention. Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

The inventors of the present invention have also found that the solubility properties of methazolamide may be improved by nanosizing thus leading to better bioavailability and dose reduction of the drug. For instance, methazolamide may be present in the form of nanoparticles which have an average particle size of less than 2,000 nm, less than 1,500 nm, less than 1,000 nm, less than 750 nm, less than 500 nm, or less than 250 nm.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

In Vitro 2-D Assay

The in vitro anti-tumor activity of methazolamide was evaluated in twelve selected human pancreatic cancer cell lines: PAXF 546L, PAXF 1986L, PAXF 1998L, PAXF 2005L, PAXF 2059L, PAXF BxPC-3, PAXF CAPAN-2, PAXF HPAC, PAXF HUP-T3, PAXF MIA-Pa-Ca-2, PAXF PA-TU-8902 and PAXF PANC-1.

PAXF 546L, PAXF 1986L, PAXF 1998L, PAXF 2005L and PAXF 2059L were established at Oncotest from the corresponding human patient derived xenograft. CAPAN-2, HUP-T3 and PA-TU-8902 were purchased from DSMZ (Braunschweig, Germany). PANC-1 was purchased from CLS Cell Line Services GmbH (Eppelheim, Germany). BxPC-3, HPAC and MIA-Pa-Ca-2 were purchased from ATCC (Rockville, Md., USA). Authenticity of cell lines was confirmed at the DSMZ by STR (short tandem repeat) analysis, a PCR based DNA-fingerprinting methodology. Cell lines were routinely passaged once or twice weekly and maintained in culture for up to 20 passages. All cells were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.1 mg/mL gentamicin (Life Technologies, Karlsruhe, Germany).

The CellTiter-Blue® Cell Viability Assay (#G8081, Promega) was used according to manufacturer's instructions. Briefly, cells were harvested from exponential phase cultures, counted and plated in 96-well flat-bottom microtiter plates at a cell density of 6,000-20,000 cells/well depending on the cell line's growth rate. After a 24 hours recovery period to allow the cells to resume exponential growth, test compounds were added. Methazolamide was applied at 10 concentrations in 1.6-fold increments in duplicate and treatment continued for 96 hours. After 96 hours treatment of cells, 20 µL/well CellTiter-Blue® reagent was added. Following an incubation period of up to four hours, fluorescence (FU) was measured by using the Enspire Multimode Plate Reader (excitation λ=531 nm, emission λ=615 nm). For calculations, the mean values of duplicate/quadruplicate (untreated control) data were used. Sigmoidal concentration-response curves were fitted to the data points (T/C values) obtained for each cell line using 4 parameter non-linear curve fit (Oncotest Warehouse Software).

Methazolamide displayed concentration-dependent activity with sigmoidal concentration-effect curves in all cell lines tested. The geometric mean absolute $IC_{50}$ value for Methazolamide was determined as 1841 µM. Individual $IC_{50}$ values were in the range from 726 µM (HUP-T3) and 5352 µM (HPAC), corresponding to 7.4-fold difference between the most sensitive and most resistant cell line. Above-average sensitive cell lines (individual $IC_{50}$ values smaller than mean $IC_{50}$ value) were shown to be HUP-T3 ($IC_{50}$=726 µM), PA-TU-8902 ($IC_{50}$=1032 µM), Mia-Pa-Ca-2 ($IC_{50}$=1524 µM) and Panc-1 ($IC_{50}$=1545 µM).

| Cell Line | Relative $IC_{50}$ µM | Absolute $IC_{50}$ µM |
| --- | --- | --- |
| PAXF 546 | 3053 | 2318 |
| PAXF 1986 | 1669 | 1850 |
| PAXF 1998 | 2226 | 2508 |
| PAXF 2005 | 1579 | 1838 |
| PAXF 2059 | 1794 | 2039 |
| PAXF BxPC-3 | 2341 | 1959 |
| PAXF CAPAN-2 | 2041 | 2029 |
| PAXF HPAC | 5508 | 5352 |
| PAXF HUP-T3 | 711 | 726 |
| PAXFMIA-Pa-Ca-2 | 1761 | 1524 |
| PAXFPA-TU-8902 | 1128 | 1032 |
| PAXF PANC-1 | 1593 | 1545 |
| Geometric Mean | 1876 | 1841 |

Example 2

In Vitro 3D Assay

Methazolamide, was investigated for anticancer activity ex vivo in 11 human tumor xenograft-derived cell suspensions or tumor cell lines of pancreatic cancer. Tests were carried out using a 3D clonogenic assay in 96-well format with image based read-out. The aim of the study was to investigate antitumor potency and tumor type selectivity of the compound. Cell lines were routinely passaged one or twice weekly. All cells were grown at 37° C. in a humidified atmosphere with 5% $CO_2$ in RPMI 1640 medium (Biochrom) supplemented with 10% (v/v) fetal calf serum and 0.1 mg/mL gentamicin. The percentage of viable cells was determined in a Neubauerhemocytometer using trypan blue exclusion.

Tumor xenografts (patient-derived, as well as cell line-derived xenografts) were passaged as subcutaneous xenografts in NMRI nu/nu mice. At a tumor volume of 400-1000 $mm^3$ tumor-bearing mice were sacrificed and tumors were collected under sterile conditions without delay according to the relevant Oncotest SOPs and the relevant animal welfare guidelines published by the FELASA and the GVSOLAS. Tumors were mechanically disaggregated and subsequently incubated with an enzyme cocktail consisting of collagenase type IV (41 U/mL), DNase I (125 U/mL), hyaluronidase type III (100 U/mL), and dispase II (1.0 U/mL) in RPMI 1640 medium (Life Technologies) at 37° C. for 60-120 minutes. Cells were passed through sieves of 100 µm and 40 µm mesh size (Cell Strainer, BD Falcon™), and washed with RPMI 1640 medium. The percentage of viable cells was determined in a Neubauer-hemocytometer using trypan blue exclusion. Aliquots of the cells were frozen down, and stored in liquid nitrogen. On each day of an experiment, a frozen aliquot of tumor cells was thawed and used for preparation of assay plates.

The clonogenic assay was carried out in a 96 well plate format using ultra low attachment plates. For each test, cells were prepared as described above and assay plates were prepared as follows: each test well contained a layer of semi-solid medium with tumor cells (50 µL), and a second layer of medium supernatant with or without test compound (100 µL). The cell layer consisted of 2.5•103 to 1•104 tumor cells per well, which were seeded in 50 µL/well cell culture medium (IMDM, supplemented with 20% (v/v) fetal calf serum, 0.01% (w/v) gentamicin, and 0.4% (w/v) agar). After 24 hours the test compounds were added after serial dilution in cell culture medium , and left on the cells for the duration of the experiment (continuous exposure, 100 µl drug overlay). Every plate included six untreated control wells and drug-treated groups in duplicate at 9 concentrations. Cultures were incubated at 37° C. and 7.5% $CO_2$ in a humidified atmosphere for 8 to 13 days and monitored closely for colony growth using an inverted microscope. Within this period, ex vivo tumor growth led to the formation of colonies with a diameter of >50 μm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 μl/well).

Methazolamide inhibited colony formation in a concentration-dependent manner with a mean relative $IC_{50}$ value of 783 μM (mean absolute $IC_{50}$ value=777 μM). Bottom plateaus of the concentration-effect curves of responding tumor models were in the range from 0 to 9%, indicating clear inhibition of tumor colony growth in the selected test range. Based on relative $IC_{50}$ values, above average activity was observed for Methazolamide against PAXF 546 cells ($IC_{50}$=336 μM).

| Cell Line | Relative $IC_{50}$ μM | Absolute $IC_{50}$ μM |
| --- | --- | --- |
| PAXF 1982 | 725 | 703 |
| PAXF 1986 | 486 | 464 |
| PAXF 2005 | 603 | 523 |
| PAXF 2059 | 754 | 820 |
| PAXF 546 | 336 | 346 |
| PAXF BxPC-3 | 808 | 837 |
| PAXF CAPAN-2 | 620 | 568 |
| PAXF HPAC | 1091 | 1365 |
| PAXF MIA-Pa-Ca-2 | 489 | 533 |
| PAXF PANC-1 | 1825 | 1756 |
| PAXF PA-TU-8902 | 2575 | 2108 |
| Geometric mean | 783 | 777 |

Example 3

In Vitro 3D Combination Assay (Methazolamide and Gemcitabine)

The clonogenic assay was carried out in a 96 well plate format using ultra low attachment plates. For each test cells were prepared as described above, and assay plates were prepared as follows: each test well contained a layer of semi-solid medium with tumor cells (50 μl), and a second layer of medium supernatant with or without test compounds (100 μl). The cell layer consisted of 2•103 to 1.25•104 tumor cells per well, which were seeded in 50 μl/well cell culture medium (IMDM, supplemented with 20% (v/v) fetal calf serum, 0.01% (w/v) gentamicin, and 0.4% (w/v) agar). The soft-agar layer was immediately covered with 90 μl of the same culture medium without agar. After 24 hour the test compounds were added after serial dilution in IMDM and transfer in cell culture medium, and left on the cells for the duration of the experiment (continuous exposure, 100 μL total drug overlay). Every plate included six untreated control wells and drug-treated groups in a layout as shown above. Cultures were incubated at 37° C. and 7.5% $CO_2$ in a humidified atmosphere for 8 days and monitored closely for colony growth using an inverted microscope. Within this period, ex vivo tumor growth led to the formation of colonies with a diameter of >50 μm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 μl/well).

Methazolamide tested as single agent inhibited colony formation of tumor cells (PAXF 1986L, PAXF 546L, PAXF Capan-2, and PAXF MIA-Pa-Ca-2) seeded in soft-agar in a concentration-dependent manner with relative $IC_{50}$ values ranging from 296.51 μM to 805.89 μM. Gemcitabine was active with relative $IC_{50}$ values ranging from 0.013 μM to 0.062 μM.

Example 4

In Vivo Animal Efficacy Study

Nude mice were subcutaneously implanted with human pancreatic cancer xenografts (PDX model PAXF 546). Tumor fragments were obtained from xenografts in serial passage in nude mice. After removal from donor mice, tumors were cut into fragments (3-4 mm edge length) and placed in PBS containing 10% penicillin/streptomycin. Recipient animals were anesthetized by inhalation of isoflurane and received unilateral or bilateral tumor implants subcutaneously in the flank.

Animals and tumor implants were monitored daily until solid tumor growth was detectable in a sufficient number of animals. At randomization, the volume of growing tumors was determined. Animals fulfilling the randomization criteria (i.e. bearing tumors of 50-200 $mm^3$, preferably 100-200 $mm^3$) were then distributed into experimental groups, aiming at comparable median and mean group tumor volumes.

Groups of eight mice were treated orally (p.o.), once daily (QD) with methazolamide at 60 mg/kg or intravenously (i.v.) once weekly (Q7D) with gemcitabine at a dose level of 50 mg/kg. Other group received combination therapy at the 60 mg/kg of methazolamide with intravenously (i.v.) once weekly (Q7D) with gemcitabine at a dose level of 50 mg/kg. The schedule of methazolamide was changed to "5-days-on-2-days-off" from day 14 onwards to improve the tolerability. The experiment was terminated on day 35.

TABLE 1

Treatment groups and schedule

| Therapy | Dose [mg/kg/day] | Schedule Day(s) | Route |
| --- | --- | --- | --- |
| Control Vehicle | 10 | 1-11, 14-18, 21-25, 28-32, 35 (h: 0) | p.o. |
| Gemcitabine | 50 | 1, 7, 14, 21, 28, 35 (h: 6) | i.v. |
| Methazolamide | 60 | 1-11, 14-18, 21-25, 2 8-32, 35 (h: 0) | p.o. |
| Gemcitabine/ Methazolamide | 50/ 60 | 1, 7, 14, 21, 28, 35 (h: 6)// 1-11, 14-18, 21-25, 28-32, 35 (h: 0) | i.v./p.o. |

The absolute tumor volumes (ATVs) were determined by two-dimensional measurement with a caliper on the day of randomization and then twice weekly. Tumor volumes were calculated according to the formula: Tumor volume=(a× b2)×0.5

Animals were weighed twice a week, or daily if body weight loss in excess of 10% was recorded. Relative body weights of individual animals were calculated by dividing the individual bodyweight on Day X (BWx) by the individual body weight on Day 0 (BW0) multiplied by 100%:
RBWx[%]=BBWWx[g]×100
  a) Mean Absolute Tumor Volume

|  | Mean Tumor volume | | | | | | | | | | |
|---|---|---|---|---|---|---|---|---|---|---|---|
|  | 1 | 3 | 9 | 12 | 15 | 18 | 21 | 24 | 28 | 31 | 34 |
| Vehicle control | 126.31 | 192.94 | 293.05 | 449.08 | 596.41 | 756.55 | 949.83 | 1165.87 | 1390.92 | 1552.30 | 1747.95 |
| Gemcitabine (50 mg/kg) | 119.84 | 172.26 | 214.28 | 262.19 | 312.84 | 334.59 | 382.57 | 454.56 | 592.69 | 648.88 | 696.91 |
| Methazolamide (60 mg/kg) | 94.47 | 121.60 | 151.64 | 189.82 | 253.64 | 341.73 | 470.79 | 583.90 | 718.08 | 836.82 | 916.02 |
| Gemcitabine (50 mg/kg) + Methazolamide (60 mg/kg) | 92.72 | 128.59 | 158.71 | 177.51 | 230.86 | 251.71 | 286.51 | 317.81 | 413.99 | 432.24 | 495.53 |

Methazolamide exhibits in vivo anti-tumor efficacy when administered orally. It inhibits tumor formation by up to 50% whereas gemcitabine when administered i.v shows inhibition of 61%. Combination of methazolamide with gemcitabine shows a significant tumor growth inhibition of 72%. Also, none of the treatment shows any significant change in body weights.

Example 5

Dosage Forms

| Ingredients | Qty/Unit (mg) | |
|---|---|---|
| Strength | 25.0 mg | 50.0 mg |
| Methazolamide | 25.00 | 50.00 |
| Dibasic Calcium Phosphate Dihydrate | 60.00 | 120.00 |
| Starch | 15.00 | 30.00 |
| Sodium starch glycolate | 5.00 | 10.00 |
| Povidone | 3.50 | 7.00 |
| Glyceryl Dibehenate | 1.50 | 3.00 |
| Total | 110 | 220 |

Methazolamide, dibasic calcium phosphate dihydrate and starch were co-sifted to give a sift. Povidone was dissolved in purified water to form the binder solution. The sift was granulated with the binder solution obtained to obtain granules which were dried and milled. The granules and pre-sifted sodium starch glycolate were blended. The resulting mixture was lubricated with pre-sifted glyceryl dibehenate and compressed to form tablets.

| Ingredients | Qty/Unit (mg) | |
|---|---|---|
| Strength | 25.0 mg | 50.0 mg |
| Methazolamide | 25.0 | 50.0 |
| HPMC K100 M CR | 18.0 | 36.0 |
| Lactose monohydrate | 29.6 | 59.2 |
| HPMC K4 M | 24.0 | 48.0 |
| Croscarmellose sodium | 3.6 | 7.2 |
| Microcrystalline Cellulose | 18.0 | 36.0 |
| Magnesium Stearate | 1.8 | 3.6 |
| Total | 120 | 240 |

Methazolamide, HPMC K100 M CR, HPMC K4 M and lactose monohydrate were co-sifted, and then granulated with a suitable granulating solvent to form granules which were dried and milled. Croscarmellose sodium, microcrystalline cellulose was sifted and mixed with the granules, which was then lubricated with pre-sifted magnesium stearate and compressed to form tablets.

| Ingredients | Qty/Unit (mg) | |
|---|---|---|
| Strength | 25.0 mg | 50.0 mg |
| Methazolamide | 25.00 | 50.00 |
| Microcrystalline Cellulose | 60.00 | 120.00 |
| Lactose monohydrate | 25.00 | 50.00 |
| Hypromellose | 4.00 | 8.00 |
| Croscarmellose sodium | 3.60 | 7.20 |
| Sodium lauryl sulfate | 0.60 | 1.20 |
| Magnesium Stearate | 1.80 | 3.60 |
| Total | 120 | 240 |

Hypromellose was dissolved in purified water to form the binder solution. Methazolamide, microcrystalline cellulose, sodium lauryl sulfate and lactose monohydrate were co-sifted, and then granulated with the binder solution to obtain the granules which were dried and milled. The granules and pre-sifted croscarmellose sodium were blended, and then lubricated with pre-sifted magnesium stearate and compressed to form tablets.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of treating pancreatic cancer comprising administering to a patient in need thereof an effective amount of methazolamide or a pharmaceutically acceptable salt thereof.

2. The method according to claim 1, wherein the pancreatic cancer is Stage 0, Stage IA, Stage IB, Stage IIA, Stage IIB, Stage III, or Stage IV.

3. The method according to claim 1, further comprising administering at least one other cancer therapy.

4. The method according to claim 3, wherein the additional cancer therapy comprises surgery, chemotherapy, immunotherapy, ablation, embolization, or ionizing radiation.

5. The method according to claim 4, wherein the additional cancer therapy comprises administering at least one additional chemotherapeutic agent comprising a nucleoside analog, antifolate, antimetabolite, topoisomerase I inhibitor, anthracycline, podophyllotoxin, taxanes, vinca alkaloid, alkylating agent, platinum compound, proteasome inhibitor, nitrogen mustard, oestrogen analogue, monoclonal antibody, tyrosine kinase inhibitor, mTOR inhibitor, retinoid, immunomodulatory agent, histone deacetylase inhibitor, or other kinase inhibitor.

6. The method according to claim 5, wherein the additional chemotherapeutic agent comprises a nucleoside analog.

7. The method according to claim 6, wherein the additional chemotherapeutic agent comprises gemcitabine, or a pharmaceutically acceptable salt thereof.

8. The method according to claim 4, wherein the additional cancer therapy comprises treatment with ionizing radiation.

9. The method according to claim 4, wherein the additional cancer therapy comprises surgery.

10. The method according to claim 1, wherein the patient has not been previously treated for pancreatic cancer.

11. The method according to claim 1, wherein the patient has undergone at least one prior treatment for pancreatic cancer.

12. The method according to claim 1, wherein the methazolamide is administered orally.

13. The method according to claim 1, wherein the methazolamide is administered in an amount from 50-500 mg/day.

14. A pharmaceutical composition comprising methazolamide and at least one other anti-cancer drug.

15. The composition of claim 14, wherein the anti-cancer drug is a nucleoside analog.

16. The composition of claim 15, wherein the anti-cancer drug is gemcitabine, or a pharmaceutically acceptable salt thereof.

17. The method of claim 1, wherein the methazolamide is provided in a kit comprising methazolamide and instructions for a dosing regimen effective to treat pancreatic cancer.

18. A kit comprising methazolamide and instructions for a dosing regimen effective to treat pancreatic cancer, and at least one other anti-cancer drug.

19. The kit of claim 18, wherein the anti-cancer drug is gemcitabine or a pharmaceutically acceptable salt thereof.

* * * * *